United States Patent
Merrill et al.

(10) Patent No.: US 6,616,982 B2
(45) Date of Patent: Sep. 9, 2003

(54) POLY(ETHYLENE OXIDE) COATED SURFACES

(75) Inventors: Edward W. Merrill, Belmont, MA (US); Susan S. Allgor, Arlington, MA (US); Gladys C. Leung, Highlands Ranch, CO (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 10/305,915

(22) Filed: Nov. 26, 2002

(65) Prior Publication Data

US 2003/0087099 A1 May 8, 2003

Related U.S. Application Data

(62) Division of application No. 08/558,232, filed on Nov. 17, 1995, now Pat. No. 6,509,098.

(51) Int. Cl.[7] .................................................. C08F 2/46
(52) U.S. Cl. ........................ 427/496; 427/164; 427/331; 427/333; 427/385.5; 427/407.1
(58) Field of Search ................................. 427/496, 164, 427/331, 333, 385.5, 407.1

(56) References Cited

U.S. PATENT DOCUMENTS

| | | |
|---|---|---|
| 4,487,808 A | 12/1984 | Lambert |
| 5,171,264 A | 12/1992 | Merrill |
| 5,275,838 A | 1/1994 | Merrill |
| 5,276,110 A | 1/1994 | Zhou et al. |
| 5,290,548 A | 3/1994 | Goldberg et al. |
| 5,308,428 A | 5/1994 | Simpson et al. |
| 5,401,327 A | 3/1995 | Ellis et al. |
| 5,509,899 A | 4/1996 | Fan et al. |

FOREIGN PATENT DOCUMENTS

| | | |
|---|---|---|
| WO | WO 91/12886 | 9/1991 |
| WO | WO 95/18840 | 7/1995 |
| WO | WO 96/09086 | 3/1996 |

OTHER PUBLICATIONS

Bayer & Stadler, "Synthesis and properties of ampiphili 'dumbell'–shaped grafted block copolymers, 1," *Macromol. Chem. Phys.* 195: 2709–2722 (1994). (No month avail.).

*Encyclopedia of Polymer Science and Engineering,* Supp. vol., pp. 647–689. (No date avail.).

Gnanou, et al., "Synthesis of star–shaped poly(ethylene oxide)," *Makromol. Chemie.* 189: 2885–2892 (1988). (No month avail.).

Harris, et al., "Laboratory synthesis of polyethylene glycol derivatives," *J. Macromol. Sci. Rev. Macro. Chem. Phys.* C25(3): 325–373 (1985). ( No month avail.).

Merrill, "Poly(ethylene oxide) star molecules: synthesis, characterization, and applications in medicine and biology," *J. Biomat. Sci. Polymer Edn* 5: 1–11 (1993). (No month avail.).

Merrill, et al., "Transformation of polymer surfaces by covalent grafting of poly(ethylene oxide) star molecules for biomedical applications," *Mit. Chem. Eng.*, 1–2. (No date avail.).

Streutwiesser & Heathcock, *Introduction to Organic Chemistry,* $2^{nd}$ ed., 1981. (No month avail.).

Teyssic & Jerome, "Naphthalene chemistry: II. A novel route for the synthesis of well defined star block copolymers displaying an A(B) architecture from hydrocarbon monomers (A) and ethylene oxide (B)," *Polymer Preprints,* 20(2): 344–348 (1979). (No month avail.).

Zhou & Roovers, "Synthesis of novel carbosilane dendritic macromolecules," *Macromolecules* 26: 963–968 (1993). (No month avail).

*Primary Examiner*—Bernard Pianalto
(74) *Attorney, Agent, or Firm*—Holland & Knight LLP

(57) ABSTRACT

Methods are provided for the fabrication of hydrophilic coatings on hydrophobic surfaces. In one embodiment, a polyethylene oxide (PEO) coating is fabricated on the surface of a polymeric material by contacting the surface with a methacrylic acid or acrylic acid monomer. The monomer first is reacted, for example by irradiation with an electron beam, to polymerize and covalently attach the monomer to the surface, to improve the hydrophilicity of the polymeric material. A coating of PEO molecules is subsequently attached to the polymer surface by hydrogen bond complexation. The PEO coating then may be covalently grafted onto the surface, for example, by irradiation grafting with an electron beam. The covalent grafting of a coating of the methacrylic or acrylic monomers to the surface greatly improves the wettability of the surface, and facilitates the covalent or non-covalent attachment of a coating of PEO to the polymer surface. Thus, hydrophilic PEO coatings can be fabricated on hydrophobic polymer surfaces, to improve the biocompatibility and other properties of the polymer surfaces.

25 Claims, No Drawings

POLY(ETHYLENE OXIDE) COATED SURFACES

CROSS-REFERENCE TO RELATED APPLICATION

This application is a divisional of U.S. Ser. No. 08/558,232 filed Nov. 17, 1995, U.S. Pat. No. 6,509,098, entitled "POLY(ETHYLENE OXIDE) COATED SURFACES" by Edward W. Merrill, Susan J. S. Allgor, and Gladys Leung.

BACKGROUND OF THE INVENTION

The present invention is generally in the area of the fabrication of poly(ethylene oxide) ("PEO") coatings on surfaces.

PEO is a polymer which has many unique properties. It is soluble in a wide variety of solvents including water, benzene and tetrahydrofuran. In organic solvents, it solvates the monovalent metal ions, $Li^+$, $K^+$ and $Na^+$. PEO is unusual in its lack of interaction with biological matter and can provide an inert surface in certain biological applications. • Merrill, E. W., *J. Biomat. Sci. Polymer Edn.*, 5:1–11 (1993). PEO is an important biomaterial because it is non-thrombogenic, i.e., it does not adsorb proteins of the intrinsic clotting system, and platelets do not adhere to it.

PEO star-shaped macromolecules are available which have many PEO chains or "arms" connected to a central body which is called the core. PEO star macromolecules can be synthesized, for example, by a living anionic polymerization using a divinylbenzene (DVB) core. • Gnanou et al., *Makromol. Chemie*, 189:2885–2892 (1988); and Merrill, *J. Biomater. Sci. Polymer Edn.*, 5:1–11 (1993).

There has been recent interest focused on the development of methods for coating surfaces with PEO. A PEO surface coating is very useful in blood-contacting devices, such as tubes and catheters, and products intended for diagnostic use, because such surfaces have the least non-specific binding to proteins and other biopolymers of any known synthetic polymer. Thus, the use of PEO coatings permits blood clotting to be minimized, and diagnostic assays to be improved.

A major problem has been the development of a thin, dense layers of PEO to cover support materials such as hard plastics, such as polyethylene terephthalate ("PETE") or flexible materials, such as silicone rubber and segmented polyurethane.

U.S. Pat. Nos. 5,171,264 and 5,275,838 to Merrill disclose that a water solution of PEO, either linear or in star form, can be cross-linked by electron irradiation to form a hydrogel layer. The hydrogel has a thickness ranging down to about 0.5 mm, which is not strongly attached to the supporting material and rather easily sheared off. Upon attachment of affinity ligands to the hydrogels, the surfaces can be used for separating and purifying therapeutic proteins.

Alternatively, PEO polymers can be attached to surfaces by hydroxyl group activation followed by chemical coupling. The terminal hydroxyl groups of the PEO molecule can chemically activated, for example, by tresyl chloride, and then attached to a surface which contains appropriate reactive groups, e.g., amino or thiol. U.S. Pat. Nos. 5,171, 264 and 5,275,838 to Merrill. There are, however, problems associated with this route. It is difficult to prepare stable surfaces having amino or thiol groups, and some procedures result in degradation of the surface to the extent that it can be readily washed off, thus providing no anchor for the PEO. Additionally, it is very difficult to implant linear PEO molecules on surfaces via this route with sufficient density to prevent the adsorption of biopolymers.

There is a need for methods for improving the hydrophilicity of hydrophobic polymer surfaces, while still maintaining the physical properties of the hydrophobic polymers. There is further a need for the development of methods for forming biocompatible coatings on surfaces. There further is a need for methods for producing hydrophilic coatings on surfaces to improve the biocompatibility of the surfaces, wherein the coatings can be readily derivatized by the attachment of biological molecules to the coating.

It is therefore an object of the invention to provide methods for the production of hydrophilic coatings on hydrophobic polymers. It is a further object of the invention to provide hydrophilic coatings on surfaces, such as PEO coatings, which reduce non-specific binding to the surfaces. It is still another object of the invention to provide methods for fabricating coatings on surfaces which can be readily derivatized by the attachment of biological molecules for use in a variety of biomedical applications.

SUMMARY OF THE INVENTION

Methods are provided for the fabrication of hydrophilic coatings on hydrophobic surfaces. In one embodiment, a poly(ethylene oxide) ("PEO") coating is fabricated on the surface of a hydrophobic polymeric material by contacting the surface with a monomer comprising an unsaturated group, such as methacrylic acid or acrylic acid. The monomer then is reacted, for example by irradiation with an electron beam, to polymerize and, as a polymer, to be covalently attached to the surface. A coating of PEO molecules then may be attached to the polymer surface by hydrogen bond complexation. The PEO coating optionally may be covalently grafted onto the surface, for example, by irradiation grafting with an electron beam. The covalent polymerization and grafting of a coating of the monomers to the surface greatly improves the wettability of the surface, and also facilitates the covalent or non-covalent attachment of a coating of PEO to the hydrophobic polymer surface. Thus, hydrophilic PEO coatings can be fabricated on hydrophobic polymer surfaces, to improve the biocompatibility and other properties of the polymers, and to provide coated polymers which can be used in a variety of different applications.

DETAILED DESCRIPTION OF THE INVENTION

Methods for the fabrication of hydrophilic coatings on hydrophobic surfaces are provided. In one embodiment, a monomer comprising an unsaturated group is grafted onto the surface, for example, by irradiation with an electron beam, to produce a polymer surface with improved wettability properties. A poly(ethylene oxide) coating then is attached to the treated surface by hydrogen bond complexation. The poly(ethylene oxide) coating then optionally may be covalently grafted onto the surface, for example, by electron beam irradiation. The poly(ethylene oxide) coatings improve the biocompatibility and hydrophilicity of the polymer surface. The surfaces may be further reacted, for example, by the attachment of a biologically active molecule, such as protein, to the surface. The polymer surfaces thus may be derivatized for use in a wide variety of biomedical applications.

Glossary of Terms

The following abbreviations are defined so that their use in this application is unambiguous:

TABLE 1

Definition of Abbreviations

| Abbreviation | Definition |
| --- | --- |
| MA | methacrylic acid (monomer) |
| PMA | poly(methacrylic acid) |
| AA | acrylic acid (monomer) |
| PAA | poly(acrylic acid) |
| NVP | n-vinyl pyrrolidone (monomer) |
| PVP | poly(n-vinyl pyrrolidone) |
| HEMA | hydroxyethyl methacrylate (monomer) |
| PHEMA | poly(hydroxyethyl methacrylate) |
| PVC | poly(vinyl chloride) |
| PVCAC | poly(vinyl chloride-co-vinyl acetate) |
| PES | poly(ether sulfone) |
| PS | polystyrene |
| PMMA | poly(methyl methacrylate) |
| PE | polyethylene |
| PE-UHMW | polyethylene, ultrahigh molecular weight |
| LDPE | low density polyethylene |
| PEG | poly(ethylene glycol) |
| PEO | linear poly(ethylene oxide) |
| STAR PEO | multi-armed molecule, with a central core and multiple PEO chains extending from the central core, wherein the PEO chains have hydroxyl temini |
| SPU | segmented polyurethane or poly(urethane-urea) |
| PDMS | poly(dimethyl siloxane) |
| $PVd_2F_2$ | poly(vinylidene fluoride) |

Monomers

Monomers comprising an unsaturated group, such as methacrylic acid or acrylic acid, can be grafted onto hydrophobic polymer surfaces to improve the hydrophilicity of the surfaces. Grafting of the monomers to the hydrophobic surfaces greatly improves the wettability properties of the surfaces, and permits the attachment of other polymers to the surfaces, to further improve the hydrophilicity, or other properties of the polymer surfaces. In one embodiment, the monomer is attached to the surface by irradiating the monomer on the surface with an electron beam, to cause polymerization and covalent attachment of the polymerized monomer on the surface as coating.

Monomers comprising an unsaturated group available in the art can be used which are capable of reacting with a hydrophobic polymer surface, to enhance the hydrophilicity of the surface, for example, by irradiation of the surface in contact with the monomer with an electron beam. Suitable monomers include: methacrylic acid and monovalent metal salts thereof, methacryloyl chloride, acrylic acid and monovalent salts thereof, acryloyl chloride, hydroxyethyl methacrylate, glycidyl methacrylate, hydroxyethyl acrylate, and hydroxypropyl acrylate.

When glycidyl methacrylate is used, the glycidyl ring must be opened to yield 1,2-dihydroxypropyl methacrylate. When acid chlorides are used, they must be hydrolyzed to the free acid. When monovalent metal salts of the acids are used, they must be converted to the free acid by rinsing with acidified water, prior to exposure to PEO. In one preferred embodiment, the monomer is methacrylic acid. The covalent grafting of methacrylic acid to hydrophobic polymer surfaces as disclosed herein greatly improves the hydrophilicity of the polymer surface, and provides a surface which can readily adsorb PEO, PEG, and Star PEO.

In one embodiment, the surface first is contacted with a water solution of a monomer, such as methacrylic acid, at a concentration of, for example, about 5–90% (w/v) in water for example, by immersing or spraying the surface. The wet surface then is exposed to electron beam irradiation on the order of about 1 to 10 megarads, to polymerize the monomer and covalently graft some of the polymer to the surface. During the reaction, the monomers polymerize, forming at least some polymer chains grafted to the support. The reaction conditions, including monomer concentration, and the dose of electron beam irradiation can be selected and optimized depending on the polymer and monomers used.

In one example of the procedure, a substrate material including a hydrophobic polymer surface of, for example, polystyrene, polyethylene, or poly(methyl methacrylate) is immersed in a shallow aqueous solution of 10 to 20% (w/v) ("weight/volume") methacrylic acid. Alternatively, the surface can be sprayed with the monomer solution. The substrate in solution then is exposed to an electron beam for a total dosage of about 2–4 megarads, thereby polymerizing and grafting the methacrylic acid to the substrate surface, to make the surface more hydrophilic.

The conditions may vary depending on the polymers and monomers used. For example, for poly(methyl methacrylate) ("PMMA") substrate surfaces, the use of about 10%–20% (w/v) methacrylic acid ("MA") and a total dose of about 4 megarads is preferred. For polystyrene surfaces, about 20% (w/v) concentration of MA and a total dose of about 4 megarads is preferred, and for polyethylene, a total dose of about 2–4 megarads and about 20% MA (w/v) can be used. The surface then may be washed with water at a pH less than or equal to about 7 to remove unbound MA and unbound polymerized MA. The methacrylic acid treated surfaces are highly wettable, holding a film of water on the surface. The appropriate conditions can be optimized for the polymer and monomer utilized. Using the method, the hydrophobic surfaces can be reacted with the monomers to form hydrophilic surfaces which have excellent, highly improved wettability.

Hydroxyethyl methacrylate (HEMA) also can be used, and can be grafted to hydrophobic polymers, to form a wettable surface, capable of binding hydrophilic polymers such as PEO molecules. HEMA can be radiation grafted, for example, onto polyethylene and polyvinylchloride acetate copolymer surfaces. After radiation, HEMA forms a viscous syrup, ultimately a gel, which is difficult to remove. Once removed by vigorous rubbing, the wettable surfaces avidly bind polyethylene oxide. In contrast, the use of methacrylic acid in water solution after extensive irradiation produces a polymer of low molecular weight which does not gel. It is possible to utilize undiluted monomer if the radiation dose is kept low, or the dose rate is kept low. Water solutions are preferred because undiluted monomer, particularly the acrylates, can undergo rapid highly exothermic reaction, leading to gelation and the formation of a tightly adherent gel layer on the hydrophobic polymer.

Other monomers which can be used include N-vinyl pyrrolidone, which renders some surfaces, such as PMMA wettable, but does not readily adsorb PEO. Acrylic acid is not very effective alone but can be used in combination with other effective monomers such as methacrylic acid. Acrylic acid in 50% solution in water, and undiluted, grafts to polyethylene after irradiation but forms a tenacious gel, so that the radiation dose must be very carefully regulated in order to achieve a smooth surface.

Polymer Surfaces

Any of a wide range of hydrophobic surfaces can be used which are capable of being grafted with monomers as disclosed herein, to improve the hydrophilicity of the polymer. Hydrophobic polymer surfaces which are generally very difficult to render hydrophilic can be rendered wettable. Exemplary polymer surfaces include polyalkylenes, such as polypropylene or polyethylene; polyarylalkylenes such as polystyrene; polyvinyls, such as poly(vinyl chloride) or poly(vinylidene fluoride); polyalkylacrylates, such as poly (methyl methacrylate), and poly(alkylene terephthalates), such as poly(ethylene terephthalate). Other exemplary polymer surfaces include polydiolefins, polysiloxanes, and flexible materials such as natural rubber, styrene-butadiene rubber, silicone rubber and polyurethanes including segmented polyurethane.

For example, polystyrene, polymethyl(methacrylate), poly(ethylene terephthalate) poly(vinyl chloride), poly (vinylidene fluoride), polyethylene, and polypropylene surfaces can be rendered water-wettable, and can be subsequently reacted to form a PEO coating, by covalently reacting monomers such as methacrylic acid with the surface by electron beam irradiation. Exemplary polyethylene polymers include low density, high density, and ultra high molecular weight polyethylene, as well as polyethylene copolymers. Other exemplary polymers include polybutadiene, synthetic polyisoprene, copolymers of butadiene and isoprene, and plasticized polyvinyl chloride.

Poly(Ethylene Oxide) Coatings

After the polymer surface has been reacted with the monomer by, for example, irradiation with an electron beam, a poly(ethylene oxide) coating may be attached to the surface either covalently or non-covalently. As used herein, the term "poly(ethylene oxide)" includes polymeric ethylene glycols such as PEO, PEG, and star PEO. In one embodiment, after reaction of the monomer with the polymer surface, poly(ethylene oxide) molecules are adsorbed to the surface to form a coating by hydrogen bonding to the hydrogen bond donor of the previously grafted monomer. In another embodiment, optionally, the PEO coating then may be covalently attached to the surface, for example, by irradiation with an electron beam.

Any of a variety of PEO polymers available in the art can be complexed with the grafted surface. For example, linear PEO or PEG with a molecular weight between about 1,000 to 5,000,000 daltons or more, may be used. Additionally, PEO star-shaped macromolecules may be used, for example, with a molecular weight of about 30,000 to 3,000,000 daltons. Star PEO molecules include a plurality of poly (ethylene oxide) arms connected to common small core, each arm having a hydroxyl at outer end. The synthesis of PEO star-shaped molecules is described, for example, in U.S. Ser. No. 08/405,149, the disclosure of which is incorporated herein by reference. In this embodiment, PEO star-shaped macromolecules with a poly 1,2-butadiene dendritic core are formed via the living anionic polymerization reaction of a poly 1,2-butadiene of narrow molecular weight distribution with ethylene oxide. The PEO star-shaped polymers produced are nearly monodisperse, have a substantially uniform number of PEO chains, and do not vary substantially in molecular weight.

If the surface has been rendered hydrophilic by grafting the monovalent metal salts of methacrylic acid or acrylic acid, the carboxylic acid must be restored by washing the surface with dilute acid (pH around 3 or lower). This step is not necessary if the acid forms of the monomers are used. If the acid chloride form of the monomer is used, the surface so treated would be washed with water to hydrolyze the acid chloride to the free carboxylic acid. The PEO solution can be applied by, for example, immersing the surface or spraying the solution. In one exemplary procedure, linear PEO with a molecular weight of 35,000 daltons is complexed to a MA treated polystyrene or MA treated PMMA surface by soaking the polymer in an aqueous solution containing about 5% (w/v) PEO for about 5 minutes. This causes the PEO to strongly complex by hydrogen bonding to the grafted surface. The surface optionally then is washed with deionized water, to remove any non-complexed PEO. This produces a surface with a coating of linear PEO bound by hydrogen bonding to the surface. The wet PEO coating on the complexed surface then may be covalently attached to the surface by, for example, exposure to electron beam irradiation, for example on the order of about 2–5 megarads. The covalent attachment of the PEO can occur via the radical reaction of the complexed PEO with the treated surface. In addition to covalent bonding of PEO to the surface, cross-linking of the PEO molecules can occur. The hydrogen bonding between the treated surface and the PEO permits the close association of the PEO to the surface, such that a high concentration of PEO molecules can be covalently grafted to the substrate surface, which has not been previously easily accomplished.

The thickness of the poly(ethylene oxide) coating may be readily controlled. For example, PEO coatings ranging from monolayers, of tens of nanometers in thickness, to multilayers on the order of 0.1 to 100 $\mu$m in thickness while wet can be formed. For example, in one embodiment, to form a thin, substantially monolayer of poly(ethylene oxide) on the grafted surface, the grafted polymer surface is contacted with poly(ethylene oxide) molecules, to adsorb the poly (ethylene oxide) molecules to the surface. Poly(ethylene oxide) molecules which are not adsorbed to the surface are then removed, for example by rinsing with water, to leave essentially a monolayer of poly(ethylene oxide) molecules adsorbed on the surface, which then is covalently grafted to the surface, to form a thin coating, essentially a monolayer of the poly(ethylene) oxide on the surface. The poly (ethylene oxide) can be in the form of PEG and star PEO as well as the higher molecular weight PEO.

In an alternative embodiment, the surface is contacted with a solution of poly(ethylene oxide) molecules, thereby to adsorb the poly(ethylene oxide) molecules to the surface, and then a thin layer of the poly(ethylene oxide) solution is left on the surface by draining the solution from the surface, but not rinsing it, to leave a multilayer of poly(ethylene oxide) molecules on the surface. The poly(ethylene oxide) molecules then are grafted to the surface, to form a thin multilayer film of poly(ethylene oxide) on the surface, for example on the order of about 0.1 to 100 $\mu$m thick while wet. The slipperyness of the multilayer film can be enhanced by using a high molecular weight poly(ethylene oxide), such as PEO with a molecular weight of one million or more.

The poly(ethylene oxide) coating preferably is covalently attached to the surface, after grafting of the monomer, by irradiation grafting with an electron beam. In one embodiment, gas permeable hard contact lenses can be derivatized with a covalent PEO coating using the method, to improve the wettability of the lenses. Gas permeable hard contact lenses such as the Boston lens, manufactured by Polymer Technology Corporation, can be coated. In this embodiment, the gas permeable hard contact lens surface is preferably first reacted electron beam irradiation with methacrylic acid monomers, to improve the hydrophilicity of the surface, and then PEO, for example of molecular weight 1,000,000, is grafted onto the treated surface by irradiation of a thin layer of its solution in water with an electron beam as described herein.

Covalent PEO coatings can be fabricated which essentially completely cover the surface. For example, coatings of linear PEO of 35,000 mol. wt. on PETE and PMMA support surfaces can be obtained wherein, by electron spectroscopy for chemical analysis ("ESCA"), using an X-ray photoelectron spectrometer, the top 30 Å to 50 Å of the coating detected is only PEO. The PEO coated materials obtained are readily wet by water and hold a film of water tenaciously. Additionally, the concentration of hydroxyl ends of the PEO on the surface, which can be used to anchor or attach to biological molecules, is very high.

Derivatization of Poly(Ethylene Oxide) Coatings

The poly(ethylene oxide) coatings, such as PEO star coatings, prevent non-specific binding of biopolymers and advantageously can be further derivatized, to improve the biocompatibility or specific binding properties of the polymer. The PEO chains in the polymer coating on the surface may be derivatized, for example, by attachment of a biomolecule or polymer thereof to the free hydroxyl groups at the termini of the PEO chains. The PEO arms on the PEO star molecules used to form the coating can serve as a molecular "leash" for biological molecules, such as antibodies, enzymes and growth factors.

Any of a range of biological molecules, such as nucleic acids, amino acids, saccharides or polymers thereof may be attached to the PEO chains of the linear or star PEO polymers bound non-covalently or covalently to a polymer surface. As used herein, the term "nucleic acids, amino acids and saccharides, or polymers" includes natural and synthetic derivatives thereof. Exemplary biological molecules which can be attached to the PEO coated surfaces include proteins including enzymes and antibodies, lipids, and polysaccharides. As used herein, the term "protein" is defined as a polymer of two or more amino acids or amino acid derivatives, such as a peptide, polypeptide or enzyme. The term "amino acid" as used herein includes amino acids and amino acid derivatives. In a further embodiment, at least two different biological molecules or polymers thereof may be covalently attached to the terminal hydroxyl groups on the PEO chains, to produce a multifunctional polymer coating on the surface. For example, two different enzymes, or an enzyme and a polysaccharide may be attached to the PEO coating.

Methods for activating the hydroxyl termini of PEO chains and then attaching a ligand, such as an antibody, to the termini are described in U.S. Pat. Nos. 5,171,264 and 5,275,838, the disclosures of which are incorporated herein by reference. For example, the free hydroxyl groups can be activated with tresyl chloride and then reacted with a ligand that contains a free amino acid or thiol group to form a covalent linkage with the ligand. • Harris, *J. Macromolecular Sci. Reviews in Macro. Chem. Phys.*, C25(3):325–373 (1985).

Applications

The hydrophobic surfaces treated with monomers as disclosed herein to improve substantially the hydrophilicity of the surfaces, and further reacted to include a poly (ethylene oxide) polymeric coating, can be used in a variety of applications. Materials forming, or coating, for example, membranes, prostheses, stents, catheters, sutures or polymeric materials, such as particles or beads can be coated to improve their hydrophilicity.

The PEO polymer coatings can be used in a wide range of biomedical applications. The PEO coatings are biocompatible, non-thrombogenic and have excellent mechanical durability. Accordingly, the PEO coatings are useful in biomedical applications for coating the surfaces of materials in which blood contact is required, such as in vivo vascular prostheses, angioplastic stents, cardiovascular sutures, metabolic support catheters, angioplastic balloon catheters, artificial hearts and ventricular assist devices. The coatings also may be used for ex vivo devices such as hemodialysis membranes and membranes for extracorporeal oxygenators.

The surface treated polymers, having improved hydrophilicity, thus may be used to coat or construct a variety of materials, such as particles, porous polymeric membranes, polymeric films and a range of biomedical devices to improve their hydrophilicity.

The materials provided with derivatized PEO coated surfaces may be used in a variety of biomedical applications. For example, the materials can be used to separate, purify and concentrate biological materials such as proteins, cells, antigens, antibodies or viruses by attaching an affinity ligand such as an antibody, $F_{ab}$ antibody fragment, Protein A, or heparin-$NH_2$ to the coating using methods disclosed in U.S. Pat. No. 5,275,838 to Merrill. The derivatized coated surfaces also may be utilized in a variety of in vivo and ex vivo biomedical devices.

In another embodiment, the hydrophilicity of gas permeable hard contact lenses can be improved by electron beam radiation grafting of the lens surface with an alkylacrylic acid such as methacrylic acid, and then of a poly(ethylene oxide) to the surface. Thus, the methods described herein can be used in a range of applications for improving the hydrophilicity and biocompatibility of hydrophobic polymer surfaces.

The present invention will be further understood by reference to the following non-limiting examples.

Equipment and Materials

In the following examples, Electron Spectroscopy for Chemical Analysis (ESCA) was carried out on a Surface Science, Inc. SSX-100 X-ray Photoelectron Spectrometer. Electron beams were generated by a 3 million electron volt Van de Graaff generator (MIT High Voltage Research Laboratory). During the distribution of energy of the electron beam, the electron flux passed through 1.5 mm glass before striking the polymeric substrate material being irradiated and the solution with which this polymeric material was in contact. The effective dose applied to the polymer at its interface with the solution was thus within ±10% of the intended dose, whether the polymer was on top of the solution (floating in some cases) or the polymer was underneath the solution. In the latter case, the depth of the solution was maintained at not more than 2–3 mm. The object treated by radiation moved under the electron beam on an continuous belt, therefore the total dose delivered was determined by the beam current in microamperes, the voltage (usually 2.5 to 3.0 million electron volts), the linear speed of the belt, and the number of times the object moved under the electron beam. Doses of electron beam irradiation are reported in megarads (1 million rads=1 megarad). One rad of adsorbed dose corresponds to 100 ergs per gram of irradiated matter. The dose rate used was between 50 000 and 100 000 rads per second. The number of passes under the beam varied. Thus, for example, a total dose of 4.0 megarads could be delivered in one pass, or in two passes of 2.0 megarads adsorbed dose in each pass, or in four passes of 1.0 megarad adsorbed dose in each pass.

In order to graft a monomer to a polymer in the examples below, the polymer sample was placed in a solution of monomer, and irradiated with a preselected dose of electron beam radiation. Solutions of monomers were made up volumetrically (volume/volume) with freshly filtered and deionized water from a MilliQ System (Millipore Corp., Bedford, Mass.). The monomer and polymer abbreviations defined in Table 1 are used in the examples. Thus, for example, 10% MA refers to a solution of 10 ml of methacrylic acid and 90 ml of water. Solutions of PEO (linear or star) were made up volumetrically—gravimetrically. Thus, 4% PEO refers to a water solution containing 4 grams of PEO dissolved in water to yield a total volume of 100 ml. Solutions of PMA and PAA in water were formed similarly to the PEO solutions. After treatment of samples with radiation, the polymer sample was rinsed well with deionized water. In some cases, if the bathing solution, such as 30% NVP, had become particularly viscous, it was found necessary to rub the surface under a stream of water between gloved fingers. If a subsequent irradiation of the same sample under a different solution was planned, the sample was air dried to remove water droplets, to prevent dilution of the new solution.

EXAMPLE 1

Wettability of Polystyrene Surfaces After Radiation Grafting

The wettability of polystyrene polymer surfaces after grafting of monomers to the surface by electron beam irradiation was tested using a variety of different monomers. A polystyrene sheet 1.2 mm thick and one inch square obtained from Goodfellow Corp., Cambridge, England (LS 121125JH) was grafted with a series of different monomers (or polymer) using solutions formulated as described above. Grafting was conducted by placing the polymer in a solution of monomer, and irradiating the polymer with a preselected dose of electron beam radiation. The wettability of the grafted polymer then was tested using the following wettability test described as follows.

Wettability Test

To test the wettability of both grafted and untreated polymer surfaces, the entire polymer surface was contacted with a fine stream of deionized water from a squirt bottle, and then the sample was allowed to drain. By this test, untreated hydrophobic polymers such as PST, PMMA, PVC, LDPE, PE-UHMW, PDMS AND SPU, shed the water film entirely, or only a few small residual spherical (sessile) droplets remained. "Excellent wettability" in the test was defined as surfaces which were completely covered by a glistening film of water after application of a water stream. A source of illumination was provided in the test, to permit liquid water films to be observed as a mirror. Wettability defined as "good" indicates initial complete coverage by water, with subsequent slow retraction from the edges of the specimen toward the center. "Fair wettability" of a surface in the test was defined as surfaces wherein, after application of the water stream, a liquid film forms over a matter of several seconds and retracts to flat puddles of significant area, but the puddles do not become sessile drops. "Poor wettability" in the test was defined as those surfaces which, after application of the water stream, shed most of the water, leaving puddles in about 1 to 2 seconds, however the puddles not become sessile drops. "Non-wettability" was found if the stream of water from the bottle did hot create a complete film of water on the surface, and the water drains from the surface in less than about a second leaving a few sessile drops or none at all.

The results of testing the wettability of polystyrene grafted with MA are shown below in Table 2.

TABLE 2

Polystyrene Surface Wettability Test, Results

| Solution | Total Dose Megarads | Number of Passes | Wettability |
|---|---|---|---|
| 20% MA | 2 | 1 | Good-Excellent |
| 20% MA | 4 | 2 | Excellent |

Grafting of the polystyrene with the following solutions gave poor or non-wettability: 10% MA irradiated with 1 megarad ("meg") or 4 meg; 20% MA with 1 meg; 10% PMA with 2 meg; and 10 or 20% AA or 10% PAA with 2 meg. Thus, acrylic acid monomer (AA) did not enhance wettability of polystyrene under these conditions, nor did the polymer solutions PMA and PAA. Monomer NVP (30% NVP at 2 meg) produces poor to fair wettability. In contrast, as illustrated in Table 2, treatment of polystyrene with methacrylic acid monomer (MA) at a concentration of 20% using a dose of 2 meg produces a surface with good to excellent wettability, while the use of increased radiation of 4 meg produces a wettable surface with excellent wettability.

EXAMPLE 2

Wettability of Poly(Methyl Methacrylate) Surfaces After Radiation Grafting

A PMMA sheet 1.2 mm thick and one inch square, obtained from Goodfellow Corp., Cambridge England, was submerged in a series of shallow monomer solutions and irradiated with an electron beam, and the wettability of the treated surfaces was tested, using the procedures described in Example 1. PMMA surfaces which were wettable were obtained using the grafting procedure as shown in Table 3.

TABLE 3

PMMA Surface Wettability Test Results

| Solution | Total Dose Megarads | Number of Passes | Wettability |
|---|---|---|---|
| 10% MA | 2 | 1 | Fair-Good |
| 10% MA | 4 | 4 | Excellent |
| 20% MA | 1 | 1 | Poor-Fair |
| 20% MA | 2 | 2 | Fair-Good |
| 20% MA | 4 | 4 | Excellent |
| 30% NVP | 2 | 1 | Good |
| 10% AA 10% MA | 2 | 1 | Fair-Good |
| 20% AA | 2 | 1 | Poor-Fair |

The following conditions gave poor or non-wettability: 10% MA using a 1 meg dose; and 10% PMA or 10% AA at 2 meg. In contrast, the use of MA at concentrations 10% or greater and under radiation doses of 2 meg or more leads to a wettable grafted layer of PMA on the PMMA surface. NVP at concentrations of 30% or more, with doses of 2 meg or more produces a wettable surface. Monomer AA is partially effective if mixed with MA, or at concentrations greater than 20%, but not as effective as MA alone.

EXAMPLE 3

Wettability of Polyethylene Surfaces After Radiation Grafting

Sheets of LDPE, 0.25 mm thick, obtained from Goodfellow Corp., Cambridge England (LS 105 455 JF) had the somewhat greasy feel of low density polyethylene. The sheets were grafted by electron beam radiation while in contact with a variety of shallow monomer solutions (2–3 mm depth), and the wettability of the grafted LDPE surface was tested. As shown in Table 4, LDPE polymer surfaces which were readily wettable were formed.

TABLE 4

Polyethylene Surface Wettability Test Results

| Solution | Total Dose Megarads | Number of Passes | Wettability |
|---|---|---|---|
| 20% MA | 2 | 1 | Excellent |
| 20% MA | 4 | 4 | Excellent |
| 10% MA; 10% AA | 2 | 1 | Fair |

The following conditions gave poor or non-wettability: 10% or 20% AA at a 2 meg dose; 30% AA at a 4 meg dose; and 30% NVP at 2 meg. In contrast, all LDPE samples treated with 20% MA had excellent wettability. These surfaces, when dry, felt glassy rather than greasy, and were diffusely reflecting. Thus MA is useful in improving the wettability of LDPE, whereas AA and NVP were not useful under the conditions tested.

To ascertain whether the effect of MA grafting is specific for LDPE, a 5 cm diameter sawn disc, 2 mm thick, of PE-UHMW, (Grade GUR 415, Hoechst Celanese), was exposed to a shallow (2–3 mm deep) layer of 20% MA under a dose of 4 megarad in 4 passes. The treated side had excellent wettability. When thoroughly dry, it felt glassy, rather than greasy, as had been observed for LDPE. Thus, reaction with MA is useful for different forms of PE to produce a wettable surface.

EXAMPLE 4

Wettability of Other Polymer Surfaces After Radiation Grafting

A one inch square piece of Millipore hydrophilic poly (vinylidene fluoride) $PVd_2F_2$ membrane (GVX, Millipore Corporation, Bedford, Mass.) was placed in a Petri dish and wet with 20% MA, then given a 2 megarad dose in one pass. The piece curled up with the duller side convex, the more shiny side concave, indicating strong grafting of PMA. Wettability was excellent. In contrast, similar treatment of a polysulfone (PES) membrane, (Millipore PES 0.2 $\mu$m membrane lot BM 12 0392 C) or of PDMS (product SE30, General Electric, Schenectady, N.Y.) did not produce a wettable surface.

A length of Tygon® type clear tubing, containing about 50% plasticizer: 50% PVC, 3⁄16" O. D.×1⁄8" I. D., was injected over a length of about 15 cm with a bolus of 20% MA, and given a dose of 4 megarad in 4 passes. The bolus was then flushed out, and the tube rinsed with deionized water. It was found that by running boluses of water through the entire tube, the bolus had a more concave meniscus in the irradiated section than in the non-treated section, indicating improved wettability and therefore some grafting of MA to form polymerized and grafted MA. Poly(vinyl chloride) (PVC) powder, obtained from Pechiney St. Gobain (mass polymerized grade Rucon® B34), was pressed into a 1 mm thick sheet in a Carver Press under a pressure of 10 000 psi at 125° (above Tg but below Tm). A piece (about 1 inch square) in a solution of 20% MA was irradiated with 2 meg in one pass. The irradiated piece became tan, and the surface in contact with MA solution became wettable (excellent wettability). In contrast, the untreated PVC was non-wettable. These results indicate that MA is concurrently grafted to PVC and polymerized, to form a hydrophilic surface which can adsorb hydrophilic molecules such as PEO.

EXAMPLE 5

Assessment of Hydrophilicity of Surfaces Grafted With Monomers and PEO

The ability of different grafted polymer surfaces to interact with and adsorb PEO molecules was tested by examining adhesion of PEO hydrogels to the surface. This assay is based on the observation that solutions in water of high molecular weight PEO, at concentration of 2% or more, of molecular weights 1 million or more, turn into networks (hydrogels) when exposed to electron irradiation in excess of about 0.5 to 1 megarad. These hydrogels thereby have a definite tensile, compressive, or shear modules. If the PEO solution is irradiated between or against a non-adsorbing surface, the hydrogel can be cleanly and easily removed in its entirety without fracture. If on the other hand, the PEO solution is contained by a surface which adsorbs PEO molecules, the results of the radiation will be to create a hydrogel layer which cannot be removed from the surface except by severe mechanical force, such as razor blade scraping. If the hydrogel layer is formed from PEO solution contained between two adsorbing surfaces, the hydrogel will become split cohesively leaving part on each surface.

LDPE Surfaces

Three LDPE sheets (about 1 inch square and 0.25 mm thick), obtained from Goodfellow Corp., Cambridge, England (LS 105 455 JF) were grafted by exposure to (a) 30% NVP, (b) 20% MA, or (c) 10% MA/10% AA under a total dose of 2 meg in one pass. Each sheet was thoroughly rinsed with deionized water to remove the polymeric solution. A 4% PEO solution (M=1×10$^6$) then was layered over the treated surfaces of (a), (b), and (c) in appropriate depth (~2 mm) and the specimens were exposed again to 2 megarads in one pass. This caused the PEO solution to form a hydrogel in contact with the treated surface. The hydrogel cleanly separated from (a), was tenaciously adhered to (b), so that it could not removed by shear without crumbling, and adhered in part to (c). Thus, grafting MA on an otherwise non-binding LDPE surface causes the surface to tenaciously adsorb PEO, so that when it is cross-linked subsequently, the hydrogel is covalently bonded to the LDPE support. In contrast, exposure to NVP and subsequent irradiation did not render the LDPE hydrophilic.

Polypropylene Surfaces

In a another evaluation of PEO hydrogel adhesion, thin layers (approximately 1 mm deep) of water solutions of the monomer, NVP (50%), AA (20%), MA (20%) or HEMA (50%) were irradiated with electron beam irradiation to between 2 and 10 megarads in polypropylene dishes (Fluoroware Inc., Chaska, Minn., Cat #H22-20-0615). Even after a radiation dose of 10 megarad, the 20% MA solution was still fluid, while the others had become firm crosslinked hydrogels. Upon pouring out the non-gelled MA solution and rinsing the polypropylene dish, the surface which had contained the MA solution was completely wettable, thus indicating that the MA solution irradiated in contact with polypropylene renders it water wettable. On the treated surfaces was poured about a 1 mm deep layer of 2% PEO solution ($M_w\sim5\times10^6$) and then the surfaces were given 2 meg of electron beam irradiation. In the untreated Fluoroware® dishes, the PEO hydrogel fell off, and no adhesion was observed. In the MA treated Fluoroware® dishes, the PEO hydrogel was strongly grafted, and crumbled under shear applied by razor scraping, leaving residue on dish. The PEO hydrogel sheared off the PVP hydrogel leaving a sticky PVP surface, and the PVP hydrogel sheared off the PP dish, leaving it hydrophobic. The PEO hydrogel also sheared off the PAA hydrogel, and the PAA hydrogel sheared off the PP dish, leaving it hydrophobic. The PEO hydrogel adhered strongly to the PHEMA hydrogel, which adhered strongly the PP dish, and when sheared off, the dish was hydrophilic. Thus, irradiation of a solution of HEMA in water on the surface rendered the PP surface wettable and strongly bonded the PEO hydrogel.

LDPE and PVC-AC Grafted With HEMA

To demonstrate the efficiency of HEMA solutions in rendering hydrophobic polymers hydrophilic, sheets (approximately 1 inch square) of LDPE (Goodfellow Corp., Cambridge, England) and of polyvinylchloride acetate copolymer (PVC-AC) were exposed to 20%, 30%, 40%, or 50% HEMA (w/v) in water in 2–3 mm deep layers, and given electron beam radiation doses of 2 and 4 megarads. Under all conditions of concentration and dose, the surfaces were rendered hydrophilic. HEMA thus is useful in forming a wettable surface, although upon rinsing of the excess with water, it forms a gum which must be removed by rubbing. The binding of the PHEMA surface to PEO was demonstrated by placing a LDPE sheet, underside grafted with PHEMA, on top of a solution of 4% ($5\times10^6$ mol. wt.) (w/v) PEO, and giving the surface a dose of 2 megarad, to turn the PEO layer into a hydrogel. Upon prying off the LDPE sheet, this hydrogel split cohesively, showing very strong bonding to the PHEMA surface.

EXAMPLE 6

Fabrication of a PEO Coating on a PETE Surface

A covalent coating of linear PEO (mol. wt. 35,000) (Fluka, Ronsonkoma, N.Y.) was fabricated on poly(ethylene terephthalate) ("PETE") sheets (about one inch square, Goodfellow Corp., Cambridge, England). The surface first was submerged in a 10% (w/v) water solution of methacrylic acid. The surface then was exposed to electron beam irradiation on the order of about 2 megarads.

Following rinsing, the surface now readily wet by water was soaked in a solution containing 5% (w/v) PEO in water for 5 minutes, to complex the PEO to the grafted poly (methacrylic acid) molecules. After draining off the PEO solution, but not thoroughly rinsing the surface, it was re-exposed to electron irradiation (2 megarads), to covalently graft PEO to the poly(methacrylic acid) grafted surface, and to crosslink the PEO. The surface was then rinsed with deionized water.

By electron spectroscopy for chemical analysis ("ESCA"), using an X-ray photoelectron spectrometer ("XPS"), the top 30 Å to 50 Å of the dry coating detected was only PEO, since only the signature for the ether carbon (—c—o—c—) was detected. In contrast, the support (PETE) shows the carbon signatures of aromatic carbon (PETE) ether carbon (PETE) and carboxyl carbon (PETE). The PETE thus treated with PEO was readily wet by water and held a film of water tenaciously ("excellent wettability").

EXAMPLE 7

Fabrication of a PEO Coating on a PMMA Surface

A PEO coating was fabricated on a poly (methylmethacrylate) ("PMMA") substrate surface (one inch square) according to the procedure as generally described in Example 6. PEO coated surfaces were obtained wherein the PEO coating completely covers the surface. By electron spectroscopy for chemical analysis ("ESCA"), using an X-ray photoelectron spectrometer, the top 30 Å to 50 Å of the coating detected is only PEO, since only the signature for the ether carbon (—c—o—c—) is detected. In contrast, the support (PMMA) shows the carbon signatures of alkane carbon (PMMA) and carboxyl carbon (PMMA). The coated surface is readily wet by water and holds a film of water tenaciously.

The procedure was conducted using two concentrations, 10 or 20% (w/v) of methacrylic acid ("MA"). The PMMA material was first immersed in an aqueous solution of 10 or 20% w/v methacrylic acid in a glass petri dish with a glass cover, and then exposed in the solution to an electron beam for a total dosage of 2 megarads, thereby polymerizing and grafting the methacrylic acid to the substrate surface. The materials were then rinsed thoroughly in water, immersed in a 5% w/v aqueous solution of PEO (mol. wt. 35,000 g/mol), removed allowing excess solution to drip from the sample, placed in clean glass petri dishes and covered with the petri dish cover, and exposed to electron beam irradiation for a total dosage of 2 megarads. For PMMA, the 10% MA solution is preferred. No loss of wettability was observed when substrate samples, after exposure to the e-beam in MA solution, were placed in water for 5 days (using 0.04 wt. % sodium azide as bacteriostat).

After the second electron beam irradiation, the PEO was grafted onto the substrate, and a hydrogel layer forms between the substrate and the glass petri dish. The hydrogel was strongly attached to the surface of the substrate. In samples that were exposed to the electron beam in only water (no MA), and then electron-beamed again after being immersed in the same PEO solution, the hydrogel layer generally peeled cleanly away from the substrate. In contrast, hydrogels formed on the samples that were treated with MA could not be cleanly scraped from the surface. In addition, XPS high resolution carbon Is scans clearly show the presence of PEO on the surface, after scraping excess hydrogel from the surface.

The hydrogen bonding between the MA on the surface and the PEO provides a close association of the PEO to the surface such that the PEO can be grafted to the substrate. This hydrogen bonding is broken if the solution is made even slightly basic such that a cation, such as $Na^+$ associates with the acid. To test the stability of the PEO layer, PEO-grafted samples were immersed in a 1 mM NaOH aqueous solution, pH 10.6, for 72 hours (using 0.04 wt. % sodium azide as bacteriostat). The samples were then rinsed thoroughly in water. The PEO hydrogel layer could still be clearly seen unchanged on the sample, and PEO remains easily detected in an XPS scan.

EXAMPLE 8

Fabrication of a PEO Coating on a Polystyrene Surface

A PEO coating was fabricated on the surface of a 1 inch square piece of polystyrene sheet (Goodfellow Corp., Cambridge, UK) according to the procedure generally described in Example 6. PEO coated surfaces were obtained wherein the PEO coating completely covers the surface.

In the procedure, two concentrations, 10 and 20% (w/v) of methacrylic acid were utilized. The substrate was disposed in the solution in a glass petri dish with a glass cover and then was exposed to an electron beam for a total dosage of 2 megarads, thereby polymerizing and grafting the methacrylic acid to the substrate surface. The materials then were rinsed thoroughly in water, immersed in a 5% (w/v) aqueous solution of PEO (mol. wt. 35,000 g/mol), removed allowing excess solution to drip from the sample, placed in clean glass petri dishes and covered with the petri dish cover, and exposed to the electron beam for a total dosage of 2 megarads. The 20% MA solution was preferred. Despite the fact that both MA solutions produce a surface that is fully wettable, XPS high resolution carbon 1s scans show a much greater presence of MA on samples e-beamed in the 20% MA solution. No loss of wettability was observed when substrate samples, after exposure to the e-beam in MA solution, were placed in water for 5 days (using 0.04 wt. % sodium azide as bacteriostat).

After the second electron beaming, PEO was grafted onto the substrate, forming a hydrogel bound to the substrate. In samples that were exposed to the e-beam in only water (no MA), and then e-beamed again after being immersed in the same PEO solution, the hydrogel layer that forms between the sample and the dish generally peeled cleanly away from the substrate, remaining fully on the glass petri dish. In contrast, hydrogels formed on the samples that were treated with MA could not be cleanly scraped from the surface after scraping. In addition, XPS high resolution carbon 1s scans clearly showed the presence of PEO on the surface. The hydrogen bonding between the MA on the polystyrene surface and the PEO provides a close association of the PEO to the surface such that a high density of PEO molecules can be grafted to the substrate.

EXAMPLE 9

Assay of PEO Binding to Surface by XPS/ESCA

The strength of binding of PEO coatings to MA-grafted polymer surfaces was tested. Methacrylic acid (MA) monomer was grafted to the polymer substrate via electron beam irradiation. The polymer was rinsed with water, thus washing off any unbound monomer, and placed in contact with an aqueous solution of PEO where the PEO hydrogen bonds with the acid moieties on the substrate surface. The samples then were rinsed or drained of excess solution, depending on whether a monolayer or multilayer of PEO was desired, and re-exposed to an electron beam, thus cross-linking the PEO and grafting it to the substrate surface. Binding of PEO to the grafted surface was assessed through chemical characterization by XPS/ESCA. A Surfaces Sciences, Inc. SSX-100 X-ray Photoelectron Spectroscope was used to determine overall atomic composition of the surface (to a depth of about 5 nm (50 Å)). In general, any atom which lies more than 10 nm (100 Å) below the surface exposed to XPS/ESCA will not emit a detectable electron signal. Thus, if a layer of grafted poly(ethylene oxide) PEO is greater than 10 nm in thickness, the only signals observed in the survey scan will be those of carbon and oxygen in the atomic ratio 2:1, and in the detailed carbon spectra the only signal (a single peak) will be that corresponding to ether carbon.

LDPE Grafted With MA

The MA treated LDPE material, after exposure to a solution of PEO ($1\times10^6$ M, 4% w/v), and rinsing with water to wash off any non-hydrogen-bonded PEO molecules, by XPS high resolution scan, showed a significant increase in the C—O peak area and subsequent drop in the C—C and C(O)O peak areas (in their contribution to the total carbon peak area) thus indicating the presence of PEO on the surface. After rinsing in 1 M NaOH for several minutes, the XPS high resolution carbon scan appeared identical to the MA treated control scans indicating removal of PEO from the surface.

PS Grafted With MA and PEO

Polystyrene (PS) grafted by electron radiation with MA and with a multilayer of PEO, was placed in a 1 mM NaOH solution, pH 10.6, for 72 hours, and then rinsed thoroughly in water. The XPS high resolution carbon is scan for the control piece of PS with MA and a thin hydrogel of PEO grafted to the surface had a dominant C—O peak, clearly showing the abundance of PEO on the surface. After 72 hours in basic solution, the PEO was still present, as shown in the XPS high resolution scan. In another test, a thick PEO hydrogel was grafted onto a MA grafted PS surface, then was mechanically scraped at the surface with flat-head tweezers, and the excess gel was scraped off the sample. The XPS scan showed that a significant layer of PEO still remained on the surface, demonstrating that it could not be completely scraped off the sample, as does result if methacrylic acid is not first grafted to the surface. This sample was then placed in 0.5 molar NaOH for 10 minutes and rinsed with water for another 5 minutes and once again analyzed in the XPS. This last treatment, as indicated by XPS high resolution scan, still did not dislodge the PEO off the surface.

Thus, PEO layers can be obtained which are strongly, covalently bound to the MA-grafted polymer surface which are not readily removed by strong base, mechanical abrasion, or excessive washing in water.

Modifications and variations of the present invention will be obvious to those skilled in the art from the foregoing detailed description. Such modifications and variations are intended to come within the scope of the following claims.

What is claimed is:

1. A method for the fabrication of a hydrophilic coating on the surface of a hydrophobic material, the method comprising:
  a) contacting the surface of a hydrophobic material with a monomer comprising an unsaturated group which is capable of reacting with the surface to enhance the hydrophilicity of the surface;
  b) reacting the monomer with the surface, thereby to enhance the hydrophilicity of the surface; and
  c) attaching poly(ethylene oxide) molecules to the hydrophilic surface of the support material, after step b), thereby to form a poly(ethylene oxide) coating on the surface.

2. The method of claim 1 wherein, in step b), the monomer is reacted with the surface by irradiation with an electron beam.

3. The method of claim 2 wherein the monomer is covalently reacted with the surface and polymerized to form a coating on the surface, in step b).

4. The method of claim 2 wherein the monomer is a selected from the group consisting of methacrylic acid, monovalent metal salts of methacrylic acid, methacryloyl chloride, acrylic acid, monovalent salts of acrylic acid, acryloyl chloride, hydroxyethyl methacrylate, glycidyl methacrylate, hydroxyethyl acrylate, and hydroxypropyl acrylate.

5. The method of claim 4 wherein the monomer is methacrylic acid.

6. The method of claim 1 wherein the hydrophobic surface comprises a polymer selected from the group consisting of polyalkylenes, polyarylalkylenes, polyvinyls, poly(alkyl methacrylates), poly(alkylene terephthalates), polydiolefins, polysiloxanes and polyurethanes.

7. The method of claim 1 wherein the surface comprises a polymer selected from the group consisting of polyethylene, polypropylene, poly(methyl methacrylate), poly(vinyl chloride), poly(vinylidene fluoride), poly(ethylene terephthalate), and polystyrene.

8. The method of claim 7 wherein the polyethylene (PE) is selected from the group consisting of high density PE, low density PE, ultra high molecular weight PE and PE copolymers.

9. The method of claim 1 wherein the surface comprises a polymer selected from the group consisting of polybutadiene, polyisoprene, copolymers of isoprene, copolymers of butadiene, silicone rubber, segmented polyurethane and plasticized polyvinylchloride.

10. The method of claim 1 wherein the hydrophobic material is selected from the group consisting of membranes, prostheses, stents, sutures, catheters, artificial hearts, ventricular assist devices, polymeric particles, and polymeric films or a coating thereon.

11. The method of claim 1 wherein step c) comprises:
 i) contacting the surface with poly(ethylene oxide) molecules thereby to adsorb the poly(ethylene oxide) molecules to the surface;
 ii) removing poly(ethylene oxide) molecules which are not adsorbed to the surface, thereby to leave essentially a monolayer of poly(ethylene oxide) molecules adsorbed on the surface; and
 iii) covalently grafting the poly(ethylene oxide) to the surface, thereby to form essentially a monolayer of the poly(ethylene) oxide on the surface.

12. The method of claim 11 wherein the poly(ethylenie oxide) molecules are covalently grafted to the surface by irradiation of the poly(ethylene oxide) molecules on the surface with an electron beam.

13. The method of claim 12 wherein the hydrophobic material is a gas permeable hard contact lens.

14. The method of claim 13 wherein the monomer is methacrylic acid.

15. The method of claim 11 wherein the PEO is selected from the group consisting of linear PEO, polyethylene glycol and a PEO star macromolecule.

16. The method of claim 15 further comprising covalently attaching terminal PEO hydroxyl groups on the surface to at least one biological molecule or polymer thereof.

17. The method of claim 15 wherein the PEO is a linear PEO with a molecular weight between about 1000 and 5,000,000 daltons.

18. The method of claim 1 wherein step c) comprises:
 i) contacting the surface with poly(ethylene oxide) molecules, thereby to adsorb the poly(ethylene oxide) molecules to the surface;
 ii) removing a portion of the poly(ethylene oxide) molecules which are not adsorbed to the surface thereby to leave a multilayer of poly(ethylene oxide) molecules on the surface; and
 iii) covalently grafting the poly(ethylene oxide) molecules to the surface, thereby to form a thin multilayer film of poly(ethylene oxide) on the surface.

19. The method of claim 18 wherein the PEO multilayer film, formed in step iii), is on the order of about 0.1 to 100 $\mu$m thick when in contact with water.

20. The method of claim 18 wherein the poly(ethylene oxide), contacted with the surface in step i), has a molecule weight of one million or greater.

21. The method of claim 18 wherein the poly(ethylene oxide) molecules are covalently grafted to the surface by irradiation of the poly(ethylene oxide) molecules on the surface with an electron beam.

22. The method of claim 21 wherein the hydrophobic material is a gas permeable hard contact lens.

23. The method of claim 18 wherein the PEO is selected from the group consisting of linear PEO, polyethylene glycol and a PEO star macromolecule.

24. The method of claim 23 wherein the PEO is a linear PEO with a molecular weight between about 1000 and 5,000,000 daltons.

25. The method of claim 23 further comprising covalently attaching terminal PEO hydroxyl groups on the surface to at least one biological molecule or polymer thereof.

* * * * *